United States Patent
Upmanue et al.

(10) Patent No.: US 10,908,677 B2
(45) Date of Patent: Feb. 2, 2021

(54) VEHICLE SYSTEM FOR PROVIDING DRIVER FEEDBACK IN RESPONSE TO AN OCCUPANT'S EMOTION

(71) Applicant: DENSO International America, Inc., Southfield, MI (US)

(72) Inventors: Vikas Upmanue, Novi, MI (US); Yu Zhang, Farmington Hills, MI (US); Bilal Alasry, Dearborn, MI (US); Te-Ping Kang, Ann Arbor, MI (US); Jordan Necovski, Livonia, MI (US); Sean Bleicher, Fenton, MI (US); Doua Vang, Waterford, MI (US); Eleanor Duke, Sterling Heights, MI (US); Nicholaus Spunar, Canton, MI (US)

(73) Assignee: DENSO INTERNATIONAL AMERICA, INC., Southfield, MI (US)

( * ) Notice: Subject to any disclaimer, the term of this patent is extended or adjusted under 35 U.S.C. 154(b) by 0 days.

(21) Appl. No.: 16/363,571

(22) Filed: Mar. 25, 2019

(65) Prior Publication Data
US 2020/0310528 A1    Oct. 1, 2020

(51) Int. Cl.
| | | |
|---|---|---|
| G06F 3/01 | (2006.01) | |
| G10L 25/63 | (2013.01) | |
| H04N 5/225 | (2006.01) | |
| G06K 9/00 | (2006.01) | |

(52) U.S. Cl.
CPC .......... G06F 3/011 (2013.01); G06K 9/00302 (2013.01); G10L 25/63 (2013.01); H04N 5/2253 (2013.01)

(58) Field of Classification Search
CPC ............................ G06K 9/00302; G10L 25/63
See application file for complete search history.

(56) References Cited

U.S. PATENT DOCUMENTS

| | | | |
|---|---|---|---|
| 6,731,307 B1* | 5/2004 | Strubbe | G06N 3/004 704/E17.002 |
| 9,688,271 B2 | 6/2017 | Chan et al. | |
| 9,771,082 B2 | 9/2017 | Farrell et al. | |
| 2009/0318777 A1* | 12/2009 | Kameyama | G01C 21/3617 600/301 |
| 2014/0136187 A1* | 5/2014 | Wolverton | G10L 15/22 704/9 |
| 2014/0172910 A1* | 6/2014 | Jung | G06F 16/68 707/769 |
| 2017/0055895 A1* | 3/2017 | Des Jardins | A61B 5/0022 |
| 2017/0061965 A1* | 3/2017 | Penilla | G10L 25/57 |
| 2018/0174457 A1* | 6/2018 | Taylor | G06K 9/00302 |
| 2018/0208209 A1 | 7/2018 | Al-Dahle et al. | |
| 2018/0357473 A1* | 12/2018 | Soma | B60W 40/00 |
| 2019/0051302 A1* | 2/2019 | Gonzalez | G10L 13/033 |

(Continued)

FOREIGN PATENT DOCUMENTS

DE    102016225222 A1    6/2018

*Primary Examiner* — Terrell M Robinson
(74) *Attorney, Agent, or Firm* — Brooks Kushman P.C.

(57) ABSTRACT

A system in a vehicle includes one or more sensors configured to obtain input from an occupant of the vehicle. The system also includes a controller in communication with the one or more sensors, wherein the controller is configured to, receive the input from the one or more sensors, determine a mood of the occupant utilizing at least the input, and output a solution to a vehicle display in response to the mood of the occupant.

20 Claims, 4 Drawing Sheets

(56) References Cited

U.S. PATENT DOCUMENTS

| | | | |
|---|---|---|---|
| 2019/0268660 A1* | 8/2019 | el Kaliouby | H04N 21/4223 |
| 2019/0279629 A1* | 9/2019 | Okamoto | G06K 9/00832 |
| 2019/0283761 A1* | 9/2019 | Bielby | G05D 1/0088 |
| 2019/0354181 A1* | 11/2019 | Woo | G06F 3/017 |
| 2020/0114834 A1* | 4/2020 | Endo | G06F 3/167 |

\* cited by examiner

VEHICLE SYSTEM FOR PROVIDING DRIVER FEEDBACK IN RESPONSE TO AN OCCUPANT'S EMOTION

TECHNICAL FIELD

The present disclosure relates to vehicle systems monitoring occupants.

BACKGROUND

A driver and passenger may communicate with one another. In certain situations, an occupant may have certain emotions or be in a certain mood. Because the driver is focusing on the road, the driver may not be aware of the situation.

SUMMARY

According to one embodiment, a system in a vehicle includes one or more microphones configured to obtain spoken dialogue from an occupant of the vehicle, a controller in communication with the one or more microphones, wherein the controller is configured to receive spoken dialogue from the microphone, determine a mood of the occupant utilizing at least the spoken dialogue, and output a solution associated with the mood on a vehicle display to a driver of the vehicle in response to the mood of the occupant.

According to one embodiment, a system in a vehicle includes one or more cameras configured to obtain facial recognition information based upon facial expressions of an occupant of the vehicle, a controller in communication with the one or more cameras, wherein the controller is configured to determine a mood of the occupant utilizing at least the facial recognition information, and output a solution associated with the mood on a vehicle display to a driver of the vehicle in response to the mood of the occupant.

According to one embodiment, a system in a vehicle includes one or more sensors configured to obtain input from an occupant of the vehicle, a controller in communication with the one or more sensors, wherein the controller is configured to, receive the input from the one or more sensors, determine a mood of the occupant utilizing at least the input, and output a solution to a vehicle display in response to the mood of the occupant.

DETAILED DESCRIPTION

Embodiments of the present disclosure are described herein. It is to be understood, however, that the disclosed embodiments are merely examples and other embodiments can take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the embodiments. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

Figure 1:
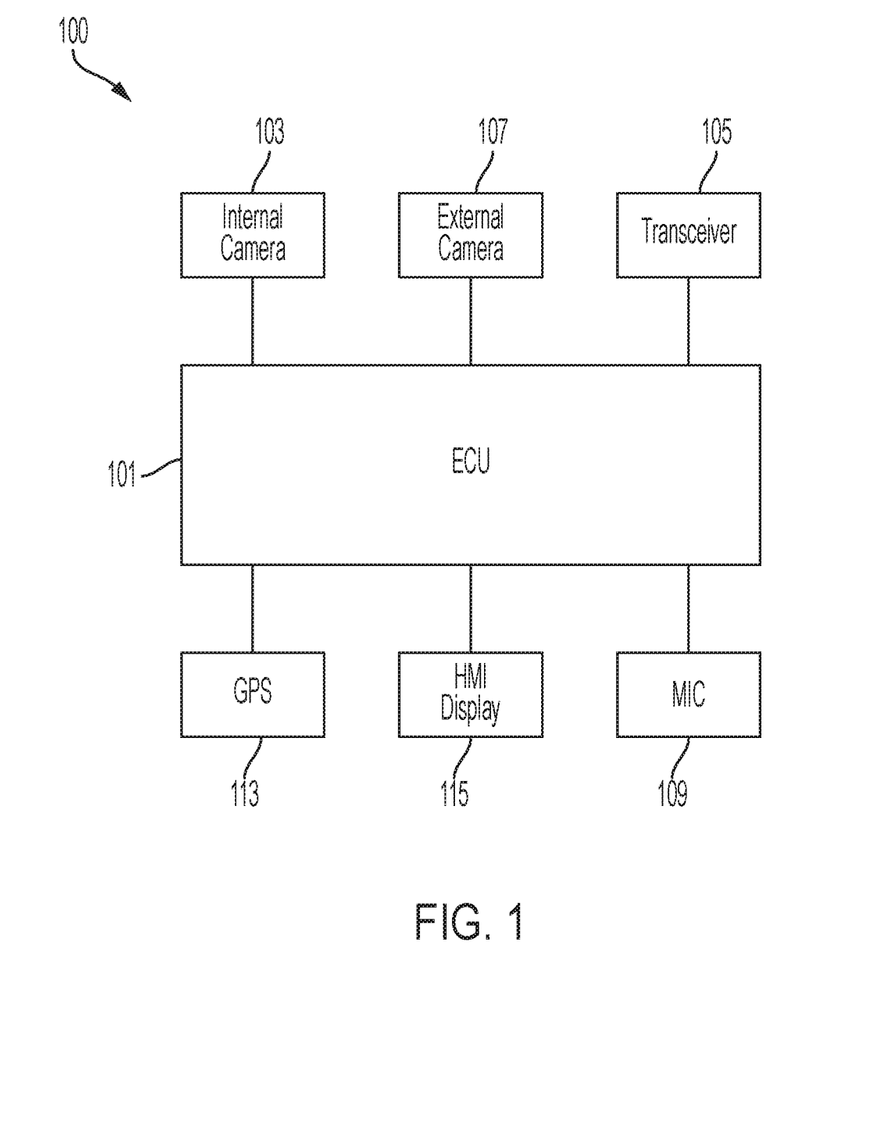
FIG. 1 illustrates an example block diagram of a vehicle system 100.

FIG. 1 illustrates an example block diagram of a vehicle system 100. The system 100 may include a controller 101. The controller 101 may be a vehicle controller such as an electronic control unit (ECU). The controller 101, also referred to herein as ECU 101, may be embodied in a processor configured to carry out instructions for the methods and systems described herein. The controller 101 may include a memory (not individually shown in FIG. 1), as well as other components specific processing within the vehicle. The controller 101 may be one or more computing devices such as a quad core processor for processing commands, such as a computer processor, microprocessor, or any other device, series of devices or other mechanisms capable of performing the operations discussed herein. The memory may store instructions and commands. The instructions may be in the form of software, firmware, computer code, or some combination thereof. The memory may be in any form of one or more data storage devices, such as volatile memory, non-volatile memory, electronic memory, magnetic memory, optical memory, or any other form of data storage device. In one example, the memory may include 2 GB DDR3, as well as other removable memory components such as a 128 GB micro SD card.

The controller 101 may be in communication with various sensors, modules, and vehicle systems both within and remote of a vehicle. The system 100 may include such sensors, such as various cameras, a LIDAR sensor, a radar sensor, an ultrasonic sensor, or other sensor for detecting information about the surroundings of the vehicle, including, for example, other vehicles, lane lines, guard rails, objects in the roadway, buildings, pedestrians, etc. In the example shown in FIG. 1, the system 100 may include an in-vehicle camera 103, a transceiver 105, a sound identification device 109, a GPS module 113, a human-machine interface (HMI) display as well as other sensors, controllers, and modules. FIG. 1 is an example system and the system 100 may include more or less sensors, and of varying types. Further, while the vehicle of FIG. 1 is shown with specific sensors in specific locations for purposes of illustration, the system 100 may be equipped with additional sensors at different locations within or on the vehicle, including additional sensors of the same or different type. As described below, such sensors may be utilized to determine a cognitive load of an occupant of the The vehicle system 100 may be equipped with a transceiver 105. The transceiver 105 may be a BLUETOOTH transceiver. In one illustrative embodiment, the system 100 uses the BLUETOOTH transceiver 105 to communicate with a user's mobile device (e.g., cell phone, smart phone, PDA, tablet, or any other device having wireless remote network connectivity). The mobile device can then be used to communicate with a network outside the vehicle system 100 through, for example, communication with a cellular tower. In some embodiments, tower may be a WiFi access point.

If the user has a data-plan associated with the mobile device, it is possible that the data-plan allows for broad-band transmission and the system could use a much wider bandwidth (speeding up data transfer). In still another embodiment, mobile device is replaced with a cellular communication device (not shown) that is installed to vehicle. In yet another embodiment, the mobile device may be a wireless local area network (LAN) device capable of communication over, for example (and without limitation), an 802.11g network (i.e., WiFi) or a WiMax network. In one embodiment, incoming data can be passed through the mobile device via a data-over-voice or data-plan, through the onboard BLUETOOTH transceiver and into the vehicle's ECU 101. In the case of certain temporary data, for example, the data can be stored on the HDD or other storage media until such time as the data is no longer needed.

In another embodiment, the transceiver 105 may be on on-board communication device or cellular modem. The on-board communication device may not require a cellular phone (e.g. mobile device) to be paired with a BLUETOOTH transceiver to communicate to an off-board server. Instead, the on-board modem may have its own capability to communicate with an off-board network.

An in-vehicle camera 103 may be mounted in the vehicle to monitor occupants (e.g. a driver or passenger) within the vehicle cabin. The in-vehicle camera 103 may be part of an occupant status monitoring system (OSM). The in-vehicle camera 103 may be utilized to capture images of an occupant in the vehicle. The in-vehicle camera 103 may obtain facial information about an occupant, such as eye-movement of the occupant and head-movement of the occupant, as discussed further below. The in-vehicle camera may be a color camera, infrared camera, or time of flight camera. The in-vehicle camera 103 may be mounted on a head rest, in the headliner, or located on a mobile device (e.g. tablet or mobile phone) to capture the driver's face, especially the driver's eyes.

A controller may receive driver status data from the OSM to determine an abnormal situation within the vehicle. The OSM employs one or more activity sensors such as a driver-facing camera, an occupant-facing camera, a health scanner, and an instrument panel to monitor activities performed by the driver or occupants (e.g. passengers in the vehicle). Based on the activity sensors, the OSM may determine whether the driver is, for example, distracted, sick, or drowsy as the abnormal situation.

A controller may receive occupant status data from the OSM to determine an abnormal situation within the vehicle. The OSM may employ one or more activity sensors such as a occupant-facing camera, a health scanner, and an instrument panel to monitor activities performed by occupants. For example, an occupant-facing camera may be employed in a vehicle headliner, vehicle headrest, or other area of the vehicle to monitor activity of the occupant. The OSM may also employ a mic that is in communication with a voice recognition (VR) engine that can detect fussiness of a child (e.g. baby) or irregular crying or sounds from the child. Based on the activity sensors, the OSM may determine whether the occupant or driver is, for example, fuss, experiencing motion sickness, hunger and fever.

A health scanner may be mounted on the vehicle seat, child seat, or suitable location which the occupant touches. The health scanner may scan the occupant's heartbeat to determine a heart rate. The OSM processes data received from the health scanner and monitors whether the occupant is suffering from a severe physical condition or episode. The OSM may also be utilized with the health scanner to see if various fluctuations in data may identify stress or issues with the occupant. The health scanner may include sensors for blood pressure monitoring, electrocardiogram (EKG/ECG) monitoring, or other body vitals.

The vehicle system 100 may include at least one external camera 107. The external camera 107 may be mounted in the rear-view mirror. The external camera 107 may also be facing out of the vehicle cabin through a vehicle's windshield to collect imagery data of the environment in front of the vehicle. The external camera 107 may be utilized to collect information and data regarding the front of the vehicle and for monitoring the conditions ahead of the vehicle. The camera 107 may also be used for imaging the conditions ahead of the vehicle and correctly detecting the positions of lane markers as viewed from the position of the camera and the presence/absence, for example, of lighting of the head lights of oncoming vehicles. For example, the external camera 107 may be utilized to generate image data related to vehicle's surrounding the vehicle, lane markings ahead, and another object detection. A vehicle may also be equipped with a rear camera (not shown) for similar circumstances, such as monitoring the vehicle's environment around the rear proximity of the vehicle.

The system may be equipped with a vehicle mic 109 or sound identification device 109. The sound identification device 109 determines a probability that the sound data corresponds to a pre-defined sound based on the subset of temporal parameters. In the illustrative embodiment, the sound identification device 109 applies an algorithm (e.g. trained deep-neural-network) to determine if an occupant event is occurring. In the illustrative embodiment, the algorithm takes a number of inputs corresponding to the number of temporal parameters. Each acoustic feature vector may include a number of features and temporal parameters that are determined for each acoustic feature. Of course, in other embodiments, the number of parameters may vary. The deep-neural-network algorithm of the illustrative sound identification device 109 may have previously been trained using machine learning in order to accurately determine if the sound data matches a pre-defined sound. The deep-neural-network algorithm may employ a softmax layer, backpropagation, and cross-entropy optimization as part of the training. This training may include supplying samples of sounds that match the pre-defined sound and samples of sounds that do not match the pre-defined sound, such as sounds similar to expected background noise. For example, if the pre-defined sound is an infant crying, the algorithm may be provided with a number of samples of infants crying as well as sounds similar to expected background noise such as adult conversation, road traffic noise, and other vehicle sounds. In some embodiments, the sound identification device 109 may determine whether the sound corresponds to several different pre-defined sounds, such as a baby crying, a baby babbling, a cough, or background sounds.

The system 100 may also include a global positioning system (GPS) 113 that detects or determines a current position of the vehicle. In some circumstances, the GPS 113 may be utilized to determine a speed that the vehicle is traveling. The system 100 may also include a vehicle speed sensor (not shown) that detects or determines a current speed that the vehicle is traveling. The system 100 may also include a compass or three-dimensional (3D) gyroscope that detects or determines a current direction of the vehicle. Map data may be stored in the memory. The GPS 113 may update the map data. The map data may include information that may be utilized with advanced driver assistance system (ADAS). Such ADAS map data information may include detailed lane information, slope information, road curvature data, lane marking-characteristics, etc. Such ADAS map information may be utilized in addition to traditional map data such as road names, road classification, speed limit information, etc. The controller 101 may utilize data from the GPS 113, as well data/information from the gyroscope, vehicle speed sensor, and map data, to determine a location or current position of the vehicle.

The system 100 may also include a human-machine interface (HMI) display 115. The HMI display 115 may include any type of display within a vehicle cabin. Such HMI displays may include a dashboard display, navigation display, multimedia display, heads-up display, thin-film transistor liquid-crystal display (TFT LCD), etc. The HMI display 115 may also be connected to speakers to output sound related to commands or the user interface of the vehicle. The HMI display 115 may be utilized to output various commands or information to occupants (e.g. driver or passengers) within the vehicle. For example, in a rear-seat occupant stress out scenario, the HMI display 115 may display message to the driver that the rear-seat occupant is stressed and need comfort. The HMI display 115 may utilize any type of monitor or display utilized to display relevant information to the occupants. The HMI display 115 may also include a heads-up display ("HUD") that is utilized to display an interface and other objects on a windshield so that the images are within a driver's periphery while driving or in an occupant's line of sight.

In addition to providing visual indications, the HMI display 115 may also be configured to receive user input via a touch-screen, user interface buttons, etc. The HMI display 115 may be configured to receive user commands indicative of various vehicle controls such as audio-visual controls, autonomous vehicle system controls, certain vehicle features, cabin temperature control, etc. The controller 101 may receive such user input and in turn command a relevant vehicle system of component to perform in accordance with the user input.

The HMI display 115 may also include a display that is embedded into a headrest of a vehicle. The HMI display 115 that is embedded into the headrest may also include a built-in camera that can face the occupant. The HMI display 115 may be facing an occupant of a vehicle (e.g. baby) to allow the occupant to interact with the HMI display or to monitor issues.

The controller 101 can receive information and data from the various vehicle components including the in-vehicle camera 103, external camera 105, the GPS 113 and the HMI display 115. The controller 101 utilize such data to provide vehicle functions that may relate to driver assistance, or autonomous driving. For example, data collected by the in-vehicle camera 103, sound identification device 109, and the forward camera 107 may be utilized in context with the GPS data and map data to provide or enhance functionality related to adaptive cruise control, automatic parking, parking assist, automatic emergency braking (AEB), etc. The controller 101 may be in communication with various systems of the vehicle (e.g. the engine, transmission, brakes, steering mechanism, display, sensors, user interface device, etc.). For example, the controller 101 can be configured to send signals to the brakes to slow the vehicle 100, or the steering mechanism to alter the path of vehicle, or the engine or transmission to accelerate or decelerate the vehicle. The controller 101 can be configured to receive input signals from the various vehicle sensors to send output signals to the display device, for example. The controller 101 may also be in communication with one or more databases, memory, the internet, or networks for accessing additional information (e.g. maps, road information, weather, vehicle information). The controller may also be utilized with the internal camera 103 to identify facial features of an occupant of the vehicle, as explained in more detail below.

Figure 2:
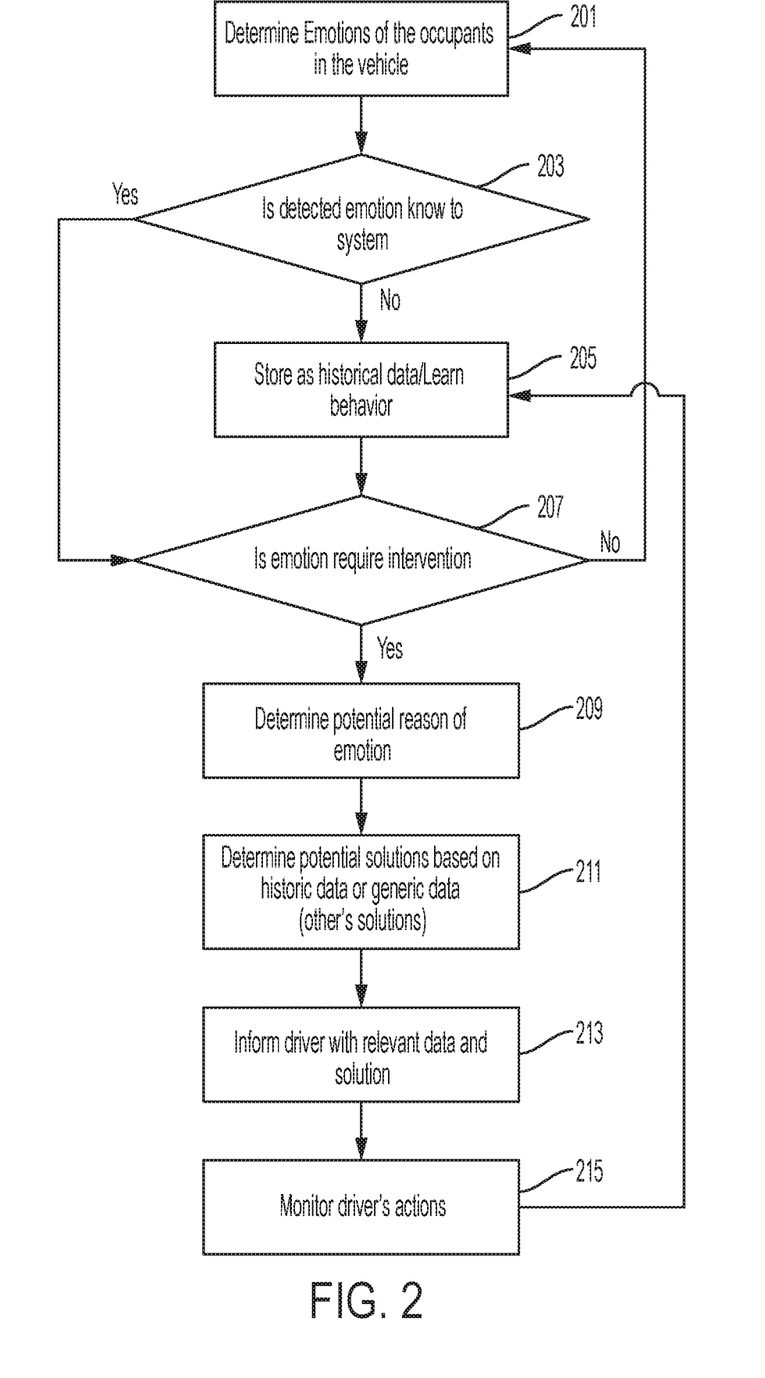
FIG. 2 is an exemplary flow chart 200 of vehicle system an occupant monitoring system identifying possible solutions based on an occupant's mood.

FIG. 2 is an exemplary flow chart 200 of vehicle system an occupant monitoring system identifying possible solutions based on an occupant's mood. At step 201, the system may utilize a OSM that constantly detects an occupant's moods or emotions. The system may utilize facial recognition cameras or other sensors to identify a mood of the user. For example, the facial recognition camera may detect smiling or other facial expressions to utilize such information to determine a mood of the occupant. The system may collect the facial recognition data and voice recognition data over time to identify and establish a normal mood for the user. For example, the system may collect such information (facial recognition and voice recognition data) over a two-week period of driving to identify a stable mood of the occupant.

At decision 203, the system will utilize such data to determine if the mood is detected from the data collected regarding the user. If the system does not recognize the mood, it may store such data as "historical data" at step 205 and attempt to learn a behavior or mood based on the data. The system will continually monitor the mood and data and compare the pattern overtime until a mood is recognizable from the data.

At decision 207, the system may recognize the mood and determine if emotional intervention is required. As shown and discussed further in FIG. 4A below, the system may have defined moods that are utilized based on the data collected from various sensors in the vehicle, such as the camera (e.g. facial recognition) and voice recognition system (e.g. microphone and voice recognition engine). The system may utilize the identification of the mood to determine if the occupant's mood/emotion requires invention. For example, the system may ask the driver to engage ins a conversation with the driver if the mood is identified as a certain way.

At step 209, the system may determine a potential reason for the emotion. The system may analyze the occupant to see if it can identify why the occupant is feeling such an emotion by further analyzing the data. For example, the system may analyze conversations that an occupant is having to identify any issues. The analysis may help the system to determine if a possible solution exists that may ease the occupant to improve the occupant's mood.

At step 211, the system may determine potential solutions based on historical data or generic data (e.g. other identified solutions). The solutions may be output onto a display and provide instructions to given to a driver. For example, in one scenario, the system may determine that the occupant is feeling neglected and wants engagement. The system may output a solution to the driver suggesting starting a conversation. The solution may be output on a display of the vehicle (e.g. an instrument panel display, heads-up display (HUD), or navigation display. In such an embodiment, the solution may include a graphical image or text for the driver to engage in a conversation. In another scenario, the solution may include audible commands given to the driver suggesting to start a conversation.

The solution that is output may be associated with a mood of the occupant. Furthermore, it may consider the identify of the driver and the passenger to determine different solutions. The system may utilize the various sensors (e.g. camera, health scanner, seat position, etc.) or driver devices (e.g. paired mobile device, key-fob, etc.) to identify the driver. The system may utilize the various sensors (e.g. camera, health scanner, seat position, etc.) or occupant devices (e.g. paired mobile device, key-fob, etc.) to identify the occupant. The solution may be responsive to the identification of the driver and the occupant. For example, the solution may consider that the occupant prefers engaging in conversation with one occupant but prefers listening to music for another occupant.

The system may also have relevant data retrieved from the occupant to identify relevant topics of conversation to discuss. For example, the system may identify through conversation by the occupant a certain subject-matter that the occupant feels engaged to discuss. The system may suggest as a part of a solution a subject-matter to discuss with the occupant. Furthermore, the system may offer feedback in the form of textual information or graphical images on the display if the conversation is not improving the mood of the occupant. The solution may also include to the driver suggestions to activate certain music, certain vehicle features (e.g. massage features, heating/cooling settings, ambient lighting, etc.).

At step 213, the system may inform the driver of relevant data and a relevant solution. The system may have a preference to adjust a setting based on the identified mood. The system may utilize historical data that compares a change of the occupant's mood and adjustment of the vehicle features to identify a success rate of the features. For example, for each mood or cluster identified in FIG. 4A, the system may monitor whether or not a proposed solution may have benefit to the occupant. The system may save the types of solutions that have helped improve the mood of the user. Thus, the system may revert to such a solution when the occupant experiences that mood again as a first attempt to improve the mood of the user.

At step 215, the system may monitor the driver's actions. The system may determine if the mood is moving to a more suitable area. The system may be constantly evaluating the occupant's mood utilizing various sensors (e.g. from facial recognition data, speech dialogue information, or body vital information, etc.) to determine the mood of the occupant. The system may compare the mood of the occupant before and after activation or adjustment. The system may utilize the comparison to determine the effectiveness of improving a mood of the occupant. The mood detection may be related to comfort and non-safety of an occupant as opposed to dealing with critical conditions of the occupant.

The system may also be able to confirm that the driver has acted out the suggested solution that is displayed to the user. For example, if the system suggests that the occupant may want to engage in a conversation with the occupant. If the driver has failed to initiate the solution after a pre-defined threshold time (e.g. 5 second, 10 seconds, 30 seconds, one minute, two minutes, etc.).

Figure 3:
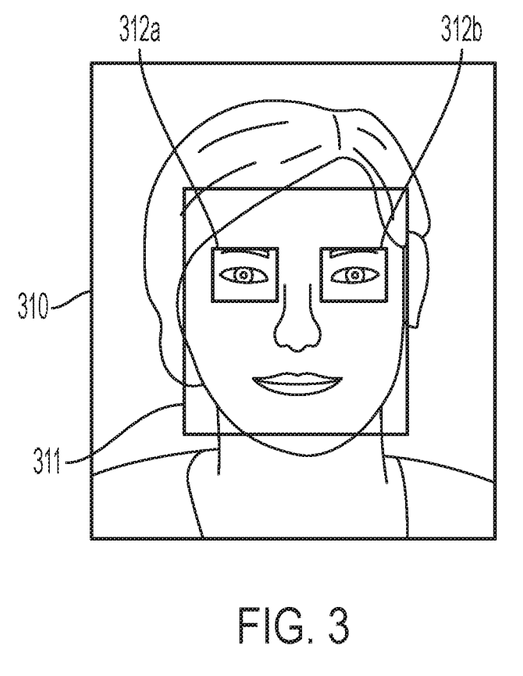
FIG. 3 illustrates an example image processing method for obtaining facial parameters from an image of a user according to this disclosure.

FIG. 3 illustrates an example image processing method for obtaining facial parameters from an image of a user according to this disclosure. The image processing method is used to obtain a facial parameter related to the user eye area, as described above with reference to the flow chart shown in FIG. 3, or is used to obtain other types of facial parameter.

As shown in FIG. 3, the image 310 is processed using a face detection algorithm to detect a face area 311 within the image, and to detect eye areas 312a, 312b within the face area 311. The pixels within the eye areas 312a, 312b then are analyzed to obtain a value of the facial parameter, as described herein.

Other examples of facial parameters that are detected from the captured image 310 include, but are not limited to, a distance parameter relating to a distance between the occupant and the display, one or more demographic parameters relating to the occupant, and a glasses parameter indicating whether the occupant is wearing glasses. The distance parameter may be used to determine whether the occupant is too close or too far from the display, either of which indicate that the occupant is experiencing viewing difficulty.

In some embodiments, a face recognition algorithm is used to detect certain types of expression or facial movements that indicate a mood of the occupant. For example, frowning, or wrinkling of the skin near the eyes may indicate a sign that the occupant is in an unsuitable mood. In such embodiments, the facial parameter includes one or more flags for different predefined facial characteristics that are indicative of a user experiencing an unsuitable mood. The value of a flag is set to 'TRUE' if that facial characteristic has been detected, and it is determined that the occupant is experiencing an unsuitable mood if a threshold number (such as one or more) of the flags in the facial parameter are set to 'TRUE'. For example, the facial parameter includes two flags relating to frowning, squinting, and wrinkling near the eyes, and if both flags are 'TRUE' it is determined that the user is experiencing an unsuitable mood.

In another embodiment, smiling or eyes being wide open may indicate a sign that the occupant is in a suitable mood. In such embodiments, the facial parameter includes one or more flags for different predefined facial characteristics that are indicative of a user experiencing a positive mood. The value of a flag is set to 'TRUE' if that facial characteristic has been detected, and it is determined that the occupant is experiencing a positive mood if a threshold number (such as one or more) of the flags in the facial parameter are set to 'TRUE'. For example, the facial parameter includes two flags relating smiling and eyes opening up, and if both flags are 'TRUE' it is determined that the user is experiencing a suitable mood.

Demographic parameters may also be utilized to help identify a mood of the user with considering other factors that may help better identify a mood of the user. The demographic parameters or data may include, for example, estimates of the occupant's age, gender, or race. Such parameters or data may be used to determine whether the user falls into any demographic categories associated with more likelihood of facing an unsuitable mood.

Figure 4:
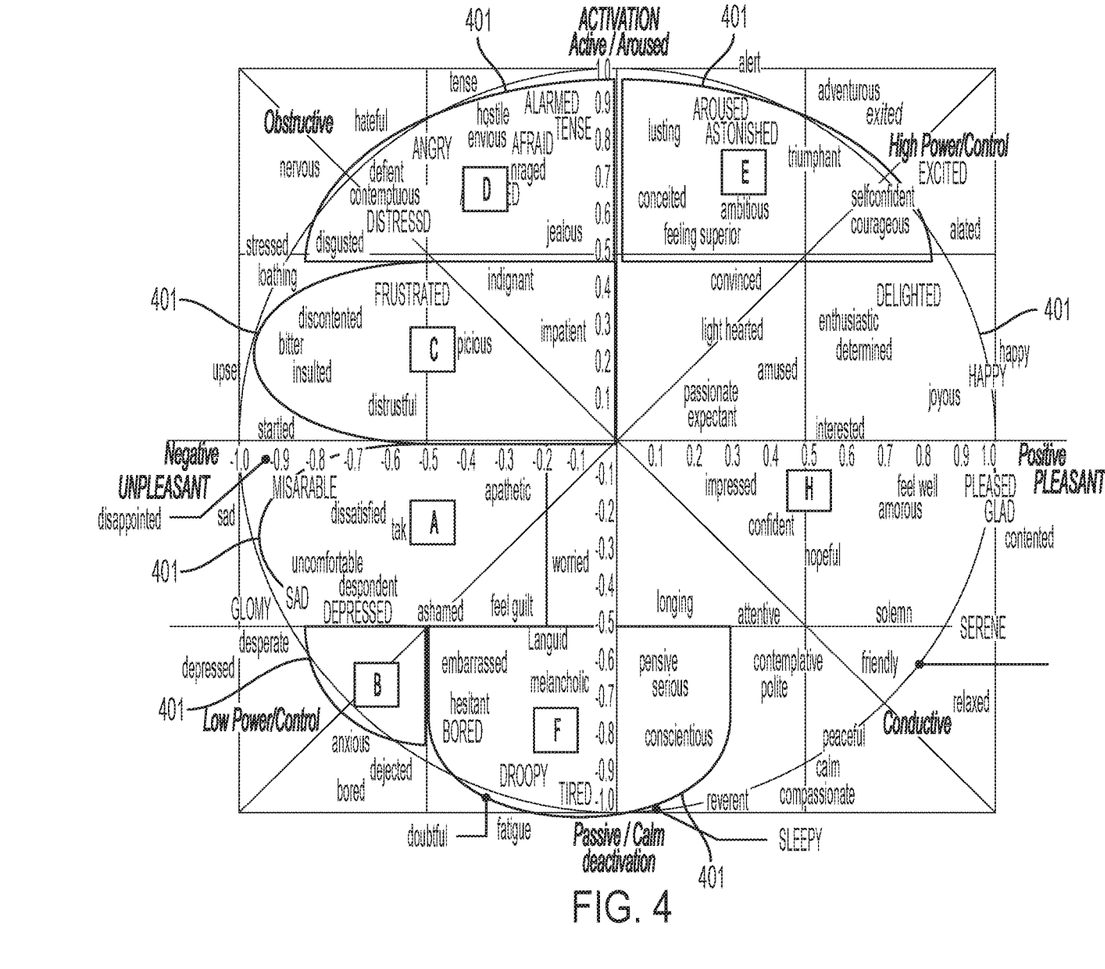
FIG. 4 illustrates an exemplary diagram of mood profiles for an occupant of a vehicle.

FIG. 4 illustrates an exemplary diagram of mood profiles for an occupant of a vehicle. FIG. 4 illustrates various moods and corresponding cluster 401 associated with the moods. There may be several moods that are found in a cluster 401. For example, a cluster A may show several moods that characterize the driver as miserable, dissatisfied, worried, sad, etc. The cluster A may be associated with "negative and low arousal." Within a cluster 401 may be various "moods" or "behavior" that are found in the cluster, as illustrated in FIG. 4A. For example, such characterizations of the mood may include miserable, dissatisfied, uncomfortable, and depressed is shown in cluster A of FIG. 4.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the invention that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to cost, strength, durability, life cycle cost, marketability, appearance, packaging, size, serviceability, weight, manufacturability, ease of assembly, etc. As such, to the extent any embodiments are described as less desirable than other embodiments or prior art implementations with respect to one or more characteristics, these embodiments are not outside the scope of the disclosure and can be desirable for particular applications.

What is claimed is:

1. A system in a vehicle, comprising:
   one or more microphones configured to obtain spoken dialogue from an occupant of the vehicle;
   a processor in communication with the one or more microphones, wherein the processor is programmed to:
   receive spoken dialogue from the microphone;
   determine a mood of the occupant utilizing at least the spoken dialogue;
   initiate an analysis of the spoken dialogue associated with the mood; and
   output a solution associated with the mood on a vehicle display to a driver of the vehicle in response to the mood of the occupant and the analysis of the spoken dialogue, wherein the solution utilizes historical data comparing a change of the mood of the occupant and adjustment of a vehicle feature, and the solution includes information identifying a topic of conversation to output to the occupant, wherein the topic of conversation indicates subject-matter that the occupant is engaged to discuss to adjust the mood of the occupant.

2. The system of claim 1, wherein the processor is further programmed to determine that the driver has conducted the solution within a pre-defined threshold time.

3. The system of claim 1, wherein the processor is further programmed to determine the mood of the occupant utilizing at least facial recognition information received from a camera of the vehicle.

4. The system of claim 1, wherein the solution includes a graphical image and text information associated with the mood of the occupant.

5. The system of claim 1, wherein the processor is further programmed to determine the mood of the occupant utilizing body vital information from one or more sensors in the vehicle.

6. The system of claim 1, wherein the processor is further programmed to determine that the mood of the occupant is changing in response to the driver conducting the solution.

7. The system of claim 1, wherein the processor is further programmed to initiate a conversation with the occupant and output music for a second occupant.

8. The system of claim 1, wherein the processor is further programmed to offer feedback including textual information or graphical images on a vehicle display when the conversation does not improve the mood of the occupant.

9. A system in a vehicle, comprising:
   one or more cameras configured to obtain facial recognition information based upon facial expressions of an occupant of the vehicle;
   a processor in communication with the one or more cameras, wherein the processor is programmed to:
   determine a mood of the occupant utilizing at least the facial recognition information and initiate an analysis of the spoken dialogue associated with the mood; and
   output a solution associated with the mood on a vehicle display to a driver of the vehicle in response to the mood of the occupant and the analysis of the spoken dialogue, wherein the solution utilizes historical data comparing a change of the mood of the occupant and the solution includes information identifying a topic of conversation to output to the occupant, wherein the topic of conversation indicates subject-matter that the occupant is engaged to discuss to adjust the mood of the occupant.

10. The system of claim 9, wherein the solution includes an input interface on the vehicle display configured to activate a vehicle feature automatically in response to activation of the input interface.

11. The system of claim 9, wherein the system further includes one or more voice recognition systems configured to obtain speech information from the occupant and utilize at least the speech information to determine the mood of the occupant.

12. The system of claim 9, wherein the solution includes text informing the driver of suggested activities.

13. The system of claim 9, wherein the solution includes text informing the driver to activate a genre of audio music.

14. The system of claim 9, wherein the solution includes text informing the driver to cease conversation with the occupant.

15. The system of claim 9, wherein the system further includes one or more sensors configured to obtain vital information of the occupant and utilize at least the vital information to determine the mood of the occupant, wherein the one or more sensors includes a blood pressure monitor or pulse monitor.

16. The system of claim 9, wherein processor is further programmed to determine that the driver has acted on the solution utilizing one or more microphones in the vehicle to determine if the occupant engaged in conversation.

17. A system in a vehicle, comprising:
   one or more sensors configured to obtain input from an occupant of the vehicle;
   a processor in communication with the one or more sensors, wherein the processor is programmed to:
   receive the input from the one or more sensors;
   determine a mood of the occupant utilizing at least the input;
   initiate an analysis of the spoken dialogue associated with the mood; and
   output a solution to a vehicle display in response to the mood of the occupant and the analysis of the spoken dialogue, wherein the solution utilizes historical data comparing a change of the mood of the occupant, and the solution further includes information identifying a topic of conversation for the processor to output for a voice session with the occupant, wherein the topic of conversation indicates subject-matter that the occupant is engaged to discuss to adjust the mood of the occupant.

18. The system of claim 17, wherein the one or more sensors includes a camera and the input from the occupant includes facial recognition information.

19. The system of claim 17, wherein the one or more sensors includes a vehicle microphone and the input from the occupant includes spoken dialogue.

20. The system of claim 17, wherein the solution includes an input interface on the vehicle display configured to activate a vehicle feature automatically in response to activation of the input interface by a driver.

* * * * *